(12) United States Patent
Chwalisz et al.

(10) Patent No.: US 6,340,688 B1
(45) Date of Patent: *Jan. 22, 2002

(54) CONTRACEPTION METHOD USING COMPETITIVE PROGESTERONE ANTAGONISTS AND NOVEL COMPOUNDS USEFUL THEREIN

(75) Inventors: Krzystof Chwalisz; Walter Elger; Karin Schmidt-Gollwitzer; Eckhard Ottow, all of Berlin (DE)

(73) Assignee: Schering Aktiengesellschaft, Berlin (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,755

(22) Filed: Sep. 17, 1998

Related U.S. Application Data

(63) Continuation of application No. 08/433,563, filed on May 3, 1995, which is a continuation of application No. 07/907,514, filed on Jul. 1, 1992, now Pat. No. 5,439,913.

(30) Foreign Application Priority Data

May 2, 1992 (DE) .......................................... 42 16 004
May 2, 1992 (DE) .......................................... 42 16 003

(51) Int. Cl.$^7$ ............................................ A61K 31/435
(52) U.S. Cl. ....................... 514/277; 514/579; 514/843; 546/344; 558/412; 558/423
(58) Field of Search .......................... 546/344; 514/277, 514/579, 843; 558/412, 423

(56) References Cited

U.S. PATENT DOCUMENTS

| | | | |
|---|---|---|---|
| 3,890,356 A | 6/1975 | Grunwell et al. | 552/651 |
| 3,928,398 A | 12/1975 | Grunwell et al. | 552/647 |
| 4,000,273 A | 12/1976 | Grunwell et al. | 514/182 |
| 4,416,822 A | 11/1983 | Campbell | 552/539 |
| 4,447,424 A | 5/1984 | Teutsch et al. | 514/179 |
| 4,609,651 A | 9/1986 | Rohde et al. | 514/179 |
| 4,670,426 A | 6/1987 | Zor et al. | 514/171 |
| 4,814,327 A | 3/1989 | Ottow | 514/179 |
| 5,262,408 A | 11/1993 | Bergink | 514/182 |
| 5,439,913 A | * 8/1995 | Chwalisz et al. | 514/277 |
| 5,516,769 A | 5/1996 | Hodgen | 514/179 |
| 5,739,125 A | 4/1998 | Kasch et al. | 514/179 |

FOREIGN PATENT DOCUMENTS

| | | |
|---|---|---|
| EP | 145493 | 6/1985 |
| EP | 129499 | 3/1988 |
| EP | 639970 | 1/1997 |
| WO | 93/21927 | 11/1993 |
| WO | 93/23020 | 11/1993 |
| WO | 94/18982 | 9/1994 |

OTHER PUBLICATIONS

Batista et al, Delayed Endometrial Maturation Induced by Daily Administration of Antiprogestin RU 486: A Potential New Contraceptive Strategy, AM J Obstet Gynecol, 167:60, 1992.
Sheth et al, A Randomized, Double–Blind Study of Two Combined and Two Progestogen–Only Oral Contraceptives, Contraception, 25:243, 1982.
Collins et al, Blockage of the Spontaneous Midcycle Gonadotropin Surge in Monkeys by RU 486, J. Clin Endocrinol Metab. 63:1270, 1986.
Danforth et al, Contraceptive Potential of RU 486 By Ovulation Inhibition III Preliminary Observations on Once Weekly Oral Administration, Contraception, 40:195, 1989.
Shoupe et al, Effects of an Antiprogesterone RU 486 in Normal Women II: Administration in the Late Follicular Phase, AM J Obstet Gynecol, 157:1421, 1987.
Liu et al, Disruption of Follicular Maturation and Delay of Ovulation After Administration of the Antiprogesterone RU 486, J Clin Endocrinol Metab, 65:1135, 1987.
Luukkainen et al, Inhibition of Folliculogenesis and Ovulation by the Antigesterone RU 486, Fert Steril, 49:961, 1988.
Messinis et al, The Effect of the Antiprogestin Mifepristone RU 486 On Maturation and In–Vitro Fertilization of Human Oocytes, BR J Obstet Gynecol, 95(6), 1988–Abstract.
Juneja et al, In Vitro Effect of RU 486 On Sperm–Egg Interaction in Mice, AM J Obstet Gynecol, 163:216, 1990.
Chwalisz et al, Inhibition of Estradiol–Mediated Endometrial Gland Formation by the Antigestagen Onapristone in Rabbits: Relationship to Uterine Estrogen Receptors, Endocrinology 129:312, 1991.
Anon, Research Disclosure 289076, 1988.
Hodgen, Surrogate Embryo Transfer Combined With Estrogen–Progesterone Therapy in Monkeys, JAMA 250:2167, 1983.
Chillik et al, Characterizing Pituitary Response to Gonadotropin–Releasing Hormone (GnRH) Antagonist in Monkeys: Tonic Follicle–Stimulating Hormone/Luteinizing Hormone Secretion Versus Acute GnRH Challenge Tests Before, During and After Treatment, Fert. Steril, 48:480, 1987.
Yoshimura et al, Progesterone Protects Oocytes From Premature Degeneration Within the Follicle, Nippon Sanka Fujinka Gakkai Zasshi, 42(9):1256, 199–Abstract.
Sakiz et al, R 2323–An Original Contraceptive Compound, Excerpta Medica, Abs. 86, 1970.

Primary Examiner—Amelia Owens
(74) Attorney, Agent, or Firm—Millen, White, Zelano & Branigan, P.C.

(57) ABSTRACT

Competitive progesterone antagonists, including two novel steroids, viz., 11β,19-[4-(cyanophenyl)-o-phenylene]-17β-hydroxy-17α-(3-hydroxyprop-1(Z)-enyl)-4-androsten-3-one and 11β,19-[4-(3-pyridinyl)-o-phenylene]-17β-hydroxy-17α-(3-hydroxyprop-1(Z)-enyl)-4-androsten-3-one, inhibit formation of endometrial glands at below their ovulation inhibiting dose and the abortive dose, and thus achieve oral contraception in females without adversely affecting the menstrual cycle and without risk of aborting a previous implanted fertilized egg or a fetus.

12 Claims, 2 Drawing Sheets

Spitz, Clinical Applications of the Antiprogestin RU 486, The Endocrinologist, 3:58, 1993.

Baulieu (1975). *Eur. J. Obstetrics, Gynaecology and Reproductive Biology 4/5*, 161–166.

Csapo et al. (1979). *J. of Steroid Biochemistry 11*, 963–969.

Baulieu(1985) "Contraceptive Activity..."in Baulieu& Segal, eds., The Antiprogestive Steroid RU486 and Human Fertility Control. pp. 179–198.

Schaism et al. (1985). *J. Clinical Endo. & Metab.* vol. *61*, pp. 484–489.

Kawano et al. *Acta Obstet. Et Gyna Japonica*, vol. 41, No. 10, Oct. 1989, pp. 1507–1511.

Chwalisz et al. (1994). "Functional Antiestrogenic Action of Progesterone..." *Current Concepts in Fertility Reg. and Repro.* Ed. Puri et al., pp. 411–428.

Ledger et al. (1992). "Inhibition of ovulation by low-dose mifepristone (RU486)" *Hum. Reprod. 7*, 945–950.

Roseff et al. "Accelerated dissolution of luteal–endomitrial integrity by the administration of antagonists of gonadotropin–releasing hormone and progesterone to late–luteal phase women" *Fertil. and Steril.54*, 805–810.

Garzo et al. (1988). "Effects of an AP (RU486) on the Hypothalamic–Hypophyseal–Ovarian–Endometrial Axis During the Luteal Phase of the Menstrual Cycle" *J. Clin. Endocrinol. Metab. 66*, 508–517.

Wolf et al. (1987). *Biol. Reprod. 36* (supp. 1), p. 109.

Steingold et al. (1992). *Sex Steroids 3*, 233–249.

Batista et al. (1991) *Am. J. Obstet. Gynecol., 165*, 82–86.

Swahn et al. (May 1990). *Hum. Reprod. 5*, 402–408.

Couzinet et al. (1990). "Late luteal admin...RU486 in normal women: effects on fertility control in long–term study" *Fertil. Steril. 54*, 1039–1044.

Wolf et al. (1990). "Tolerance of perinidatory primate embryos to RU486 exposure in vitro and in vivo" *Contraception 41*, 85–93.

Spitz et al. (1989). "Progesterone Antagonists on the Horizon" *Clinical Obstetrics and Gyecology 32*, 403–413.

van Uem et al. (1989). *Contraception 40*, 171–184.

Wolf et al. (1989). *Fertility and Sterility 52*, 1055–1060.

Spitz et al. (1989) "Response to...RU486 during early pregnancy ..." *J. Repro Fertil Suppl. 37*, 253–260.

Yen et al. (1987). Luteal Contraception *Contraception* Suppl. to vol. *36*, 13–25.

Neiman et al. (1988) *Bailliers Clin. Obst. and Gyn. 2*, 609–616.

Neulen et al. (1987)*Acta Endocrinol.* [suppl]. *114*, 7–8.

Ulmann et al. (1987). *Hormone Research 28*, 274–2714.

Nieman et al. (1987). *N.E. J.Med. 316*, 187–191.

Agoestina (1987). *Contraception 36* Supp. 33–38.

Elger et al. (1986). *J. Steroid Biochem. 25*, 835–845.

Baulieu et al. (1986). *Human Reproduction 1*, 107–110.

Strecke et al. (1983). *Experimental and Clinical Endocrinology 81*, 122–136.

* cited by examiner

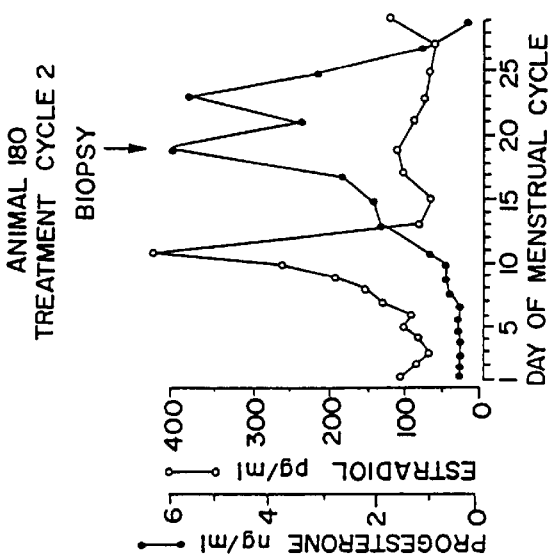
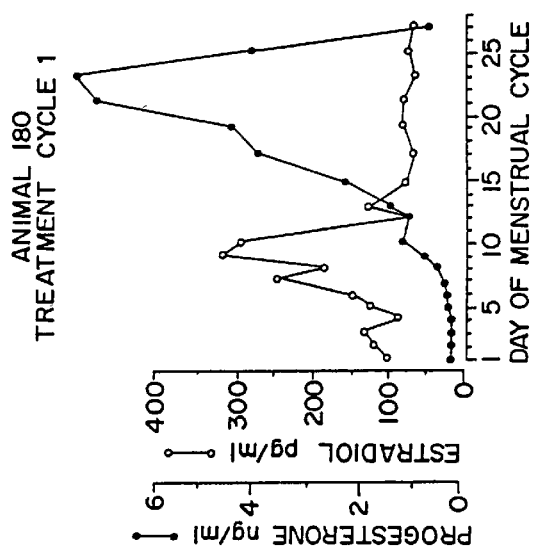
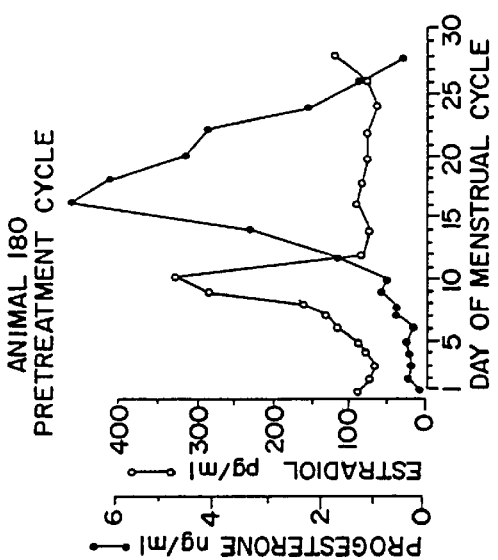

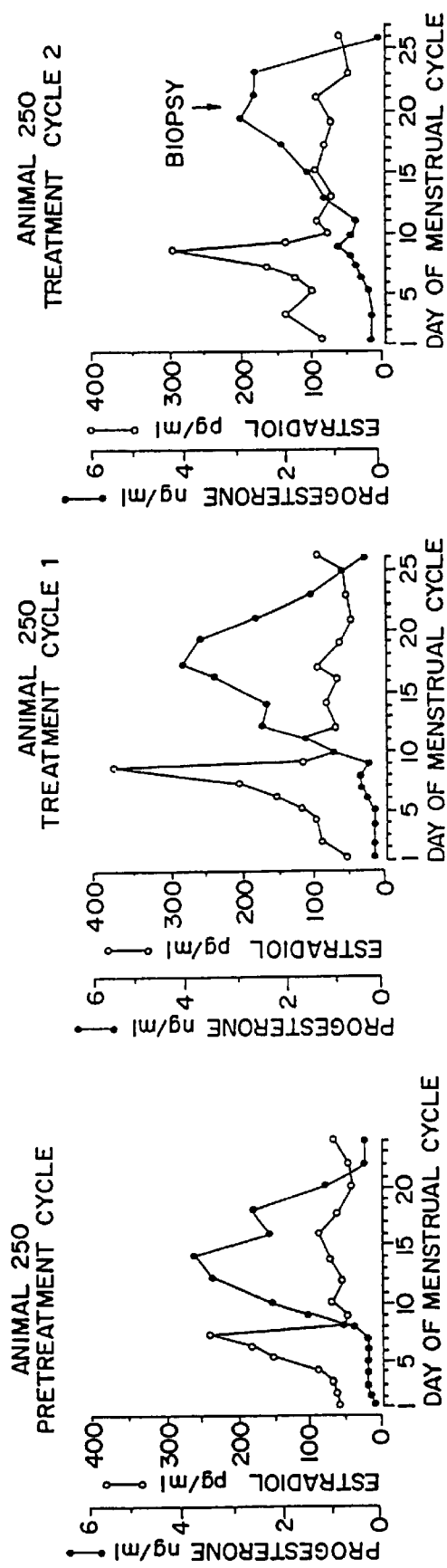

US 6,340,688 B1

CONTRACEPTION METHOD USING COMPETITIVE PROGESTERONE ANTAGONISTS AND NOVEL COMPOUNDS USEFUL THEREIN

This is a continuation, of application Ser. No. 08/433,563 filed May 3, 1995, which in turn is a continuation of application Ser. No. 07/907,514 filed Jul. 1, 1992 now U.S. Pat. No. 5,439,913.

BACKGROUND OF THE INVENTION

This invention relates to a novel contraceptive method employing a competitive progesterone antagonist and to novel progesterone antagonists useful therein.

By inhibiting the formation of endometrial glands and epithelium growth, the implantation of a fertilized egg in the uterus is rendered impossible (inhibition of the uterine receptivity). The employment of competitive progesterone antagonists according to the invention can thus be used for contraception in the female.

RU 486 (11β-[4-N,N-(dimethylamino)phenyl]-17β-hydroxy-17α-propinyl-estra-4,9(10)-dien-3-one; EP-A-0057115) and other 11β-aryl or 11β,19-arylene-substituted steroids are compounds which can displace progesterone and the glucocorticoids from their respective receptors. These substances are pharmacologically distinguished by strong progesterone- and glucocorticoid-antagonistic effects. These properties determine their previously practiced therapeutic uses. RU 486 is useful, e.g., as a progesterone antagonist for therapeutic termination of pregnancy and also as a glucocorticoid antagonist for treatment of Cushing's syndrome in the wake of a pathologically increased secretory activity of the suprarenal cortex. The abortive dose of RU 486 is 200–600 mg in the female.

It has also long been known that competitive progesterone antagonists are able to inhibit ovulation in various animal species and in the human female. (Collins et al., "Blockade of the spontaneous mid-cycle gonadotropin surge in monkeys by RU 486; A progesterone antagonist or agonist", J. Clin. Metab., 63:1270–1276 (1986);

Croxatto, H. B., "Salvatierra 1990 Cyclic use of antigestagens for fertility control", IIIrd International Symposium on Contraception, Heidelberg, Jun. 19–23, 1990;

Danford et al., "Contraceptive potential of RU 486 by ovulation inhibition. III. Preliminary observations on once weekly administration", Contraception 40: 195–200 (1989);

Kekkonen et al., "Lähteoenmäki P 1990 Interference with ovulation by sequential treatment with the antiprogesterone RU 486 and synthetic progestin", Fertil Steril [Fertile Sterile] 53,4747;

Puri et al., "Gonadal and pituitary responses to progesterone antagonist ZK 98 299 during the follicular phase of the menstrual cycle in bonnet monkeys", Contraception 39, 2: 227–243 (1989);

Puri et al., "Contraceptive potential of a progesterone antagonist ZK 98 734: Effect on folliculogenesis, ovulation and corpus luteum function in bonnet monkeys". In Moudgal et al., (eds) (1990);

U.S. Pat. No. 4,764,513 teaches that the receptivity of the endometrium for implantation (implantation window) can be shifted (delayed) by administering a competitive progesterone antagonist to a female to increase the likelihood of successful implantation of an in vitro fertilized egg.

11β,19-o-Phenylene-bridged steroids, which exhibit especially strong competitive progesterone-antagonistic effectiveness in the case of considerably reduced anti-glucocorticoid activity relative to the comparison compound 11β-(4-dimethylaminophenyl)-17β-hydroxy-17α-(propin-1-yl)-4,9(10)-estradien-3-one (RU 486; EP-A-0 057 115), are described for the first time in U.S. Pat. No. 5,095,129. The novel compounds of this invention (Compounds I and II) fall within the scope of the generic formula of U.S. Pat. No. 5,095,129, but are not disclosed therein by name or by example.

The dose of a competitive progesterone antagonist having an ovulation inhibition effect depends greatly on the species thereof employed. In the case of RU 486, it is 50–100 mg in the human female. (Croxatto et al.; loc. cit., Ledge et al. (1992) Inhibition of ovulation using very low dose mifepristone; Abstract: Second Congress of the European Society of Contraception. RU 486 shows little or no dissociation of its central and endometrial effects in humans (Ledge W. L. et al., Terra Symposium on Progesterone Antagonists, May 25–29, 1992, Mohouk, N.Y.).

An "LH+2" treatment for implantation inhibition has been proposed (Swahn et al., "The effect of RU 486 administration during the early luteal phase on bleeding pattern, hormonal parameters and endometrium," *Human Reproduction* 5, 4:402–408 (1990)): 2 days after the LH peak (LH= Luteinizing Hormone) in the menstrual cycle (occurrence of the LH peak corresponds to the time of ovulation) of the female (i.e., thus on day 14, 15 or 16), an ovulation-inhibiting dose of RU 486 is administered one time. The active compound is thus administered only after the time of ovulation in the luteal phase of the menstrual cycle (luteal contraception).

It was only recently reported that an endometrial desynchronization in the female without hormonal changes (progesterone and estradiol concentrations) can be achieved by the competitive progesterone antagonist RU 486, when the latter was administered on day 5 and day 8 after the occurrence of the LH peak in the menstrual cycle (dosage in each case 10 mg, peroral) (Kettel et al., 1992). Reliable conception without ovulation inhibition cannot be achieved if a competitive progesterone antagonist is administered only after LH peaks in the menstrual cycle is achieved.

It has now been found that in accordance with this invention, competitive progesterone antagonists are capable, at a dosage regime which does not inhibit ovulation or induce abortion, of inhibiting the formation of endometrial glands in the proliferation phase as well as the function of the glands in the luteal phase of the menstrual cycle, thereby achieving contraception, if the administration of the dose takes place at least once before and optionally also after the occurrence of the LH peak.

SUMMARY OF THE INVENTION

In a method aspect, this invention relates to a method of contraception in a female, which comprises administering thereto during the follicular phase of her menstrual cycle and optionally also in the luteal phase thereof an amount of a competitive progesterone antagonist, which is less than an ovulation-inhibiting and less than an abortion-inductive dose and which is effective to inhibit the formation of endometrial glands, which glands are a requirement for the implantation of a fertilized egg in the uterus.

In a composition aspect, this invention relates to an 11β,19-o-phenylene-17β-hydroxy-17α-(3-hydroxyprop-1 (Z)-enyl)-4-androsten-3-one of the formula:

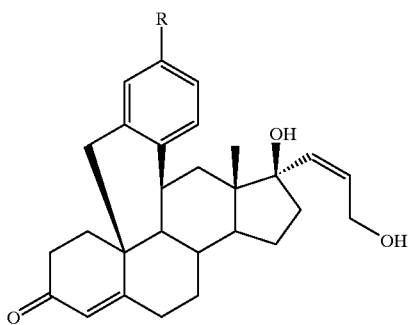

wherein R is

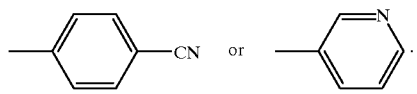

In another composition aspect, this invention relates to a pharmaceutical composition comprising in admixture with a pharmaceutically acceptable carrier, an amount per unit dosage of a competitive progesterone antagonist which is less than an ovulation-inhibiting and less than an abortion-inductive dose and which is effective to inhibit the formation of endometrial glands and epithelium growth.

DETAILED DISCUSSION

In the proliferation phase, an estrogen-induced formation of the secretory glands in the endometrium occurs in the normal menstrual cycle, while in the luteal phase (also designated as the secretion phase), the secretory activity of the glands is induced by progesterone. The described effect of the competitive progesterone antagonists in the proliferation phase, i.e., before ovulation, thus is not inherently based on a progesterone inhibition effect, since the proliferation of the endometrial glands is estrogen-dependent. Further, the progesterone concentrations in the blood in the proliferation phase of the menstrual cycle are very low. By the use of competitive progesterone antagonists according to the invention, a selective inhibition of the uterine receptivity is achieved without adversely influencing the menstrual cycle and at doses too low to induce abortion if ovum implant has already occurred.

The ability to achieve contraception at lower than abortion-inducing doses and ovulation inhibiting doses is a very important consideration for some human females who are opposed to abortion or are concerned about the long-term medical effects of ovulation inhibition.

A decisive advantage of the use proposed here exists in the very high contraceptive reliability of the progesterone antagonist employed, since the endometrium is not capable to receive a fertilized egg when a respectively very low dosage of the competitive progesterone antagonist is administered before and optionally after the ovulation. An implantation is also not to be ruled out in the proliferation phase of the normal menstrual cycle. Since the endometrial glandular secretions are essential for endometrial receptivity, a successful implantation is impossible in the case of an atrophy of the endometrial glands and epithelium. As a result, contraceptive reliability is also assured in females with an irregular menstrual cycle.

Two novel competitive progesterone antagonists, viz., 11β,19-[4-(4-cyanophenyl)-o-phenylene]-17β-hydroxy-17α-(3-hydroxyprop-1(Z)-enyl)-4-androsten-3-one (I) and 11β,19-[4-(3-pyridinyl)-o-phenylene]-17β-hydroxy-17α-(3-hydroxyprop -1(Z)-enyl)-4-androsten-3-one(II) have surprisingly pronounced peripherally selective effectiveness, i.e., the effect of compounds I and II on the endometrium is very greatly pronounced, while at the same dose, at most only a slight central effect is observed on the hypophysial-ovarian axis.

Such competitive progesterone antagonists can also be designated as dissociated, since at a specific threshold dose, although changes of the endometrium are observed, ovulation (central effect) is not inhibited. The ratio of ovulation-inhibiting dose and implantation inhibiting dose (dissociation factor) (as determined in the rat after peroral administration) can be used as a measurement of the dissociation. This ratio varies from species to species but is at least about 30 or higher in a dissociated or competitive progesterone antagonist.

An advantage of dissociated or competitive progesterone antagonists lies in the fact that they can be administered at doses high enough to achieve endometrial effects without inhibiting ovulation. As a result, a normal menstrual cycle is maintained.

The competitive progesterone antagonists are preferably administered as individual spaced dosage units, e.g., preferably at 4 to 10 days in regular intervals, e.g., every week of the menstrual cycle, each at a dose which is insufficient to inhibit ovulation or to induce abortion if implantation has already occurred. On the other hand, a similar effect on endometrial receptivity can be achieved with lower once-daily oral doses. The use of slow release systems (microcrystalline suspensions, transdermal patches and subcutan implants) is also possible, provided the amount of progesterone antagonist released therefrom is sufficient to inhibit ovum implantation during the predicted life of the system but lower than the dose which interferes with any ovulations which would otherwise have occurred during that period of time.

The above-described use of competitive progesterone antagonists is evidenced by tests performed with Onapriston [11β-(4-dimethylaminophenyl)-17α-hydroxy-17β-(3-hydroxypropyl)-13α-methyl -4,9-gonadien-3-one; EP-A-0129499], a typically competitive progesterone antagonist, on adult, female bonnet monkeys (*Macaca radiata*).

The test design is set forth below:

| | |
|---|---|
| bonnet monkeys: | adult female animals, body weight 3.5–4.5 kg |
| groups treated with Onapriston (N = 3): | 5 mg and 10 mg per animal per group subcutaneously on an oily base (benzyl benzoate/castor oil 1:10) |
| beginning of treatment and diagram of treatment: | day 1 of the menstrual cycle, then administration in one-week intervals |
| duration of treatment: | 2 cycles |
| vehicle control (N = 3): | 1 ml |
| collection of blood samples: | 1 × daily for the first 10 days of the respective menstrual cycle and then every 2 days; also in the pretreatment and aftertreatment cycle |
| endometrial histology: | the biopsies were performed under ketamine anesthesia (10 mg/kg of body weight) on day 20 of the second cycle, i.e., |

-continued

| hormonal determinations: | after 7 administrations of the progesterone antagonist progesterone and estradiol were determined with a radioimmuno-assay (RIA) |
|---|---|

Observations relative to the changes of the endometrium and the hormone level:

Table 1 shows that both the length of the cycle and the menstrual period relative to the control group are not changed by the treatment according to the invention.

The estradiol and progesterone levels clearly show that the folliculogenesis and ovulation has occurred normally in all animals: normal preovulatory estradiol peak, normal progesterone level in the luteal phase (FIG. 1).

The histology shows that in contrast to control animals, the endometrium was atrophied in both treatment groups. Especially affected were the endometrial glands: atrophic and inactive glands with an increase of the stromal tissue.

11β-[(4-N,N-dimethylamino)-phenyl]-17aβ-hydroxy-17aα-propinyl-D-homo-4,9(10),16-estratrien-3-one (all disclosed in EP-A-0 057 115);

11β-p-methoxyphenyl-17β-hydroxy-17α-ethinyl-4,9 (10)-estradien-3-one (Steroids 37 (1981), 361–382), and 11β-(4-acetylphenyl)-17β-hydroxy-17α-(prop-1-inyl)-4, 9(10)-estradien-3-one (EP-A 0 190 759); and the 11β-aryl-14β-estradienes and estratrienes described in EP-A 0 277 676, the 19,11β-bridged steroids, which are the subject of U.S. Pat. No. 5,095,129, the 11β-aryl-6-alkyl (or 6-alkenyl or 6-alkinyl)-estradienes and pregnadienes known from EP-A 0 289 073 and the 11β-aryl-7-methyl (or 7-ethyl)-estradienes known from EP-A 0 321 010 as well as the 10β-H steroids of EP-A 0 404 283. This list is not complete as other competitive progesterone antagonists described in the above-mentioned publications as well as those of publications not mentioned here are also suitable.

For use according to this invention, especially suitable are those competitive progesterone antagonists which are peripherally selectively effective, i.e., in which the endometrial effect is pronounced, at a dose at which at most only a slight central effect is observed on the hypophysial-ovarian axis.

TABLE 1

Effect of the vehicle and of Onapriston on the length of the menstrual cycle (MC) and the menstrual period (MP) of bonnet monkeys*

| | Pretreatment Cycle | | Treatment Cycle 1 | | Treatment Cycle 2 | | After-treatment Cycle | |
|---|---|---|---|---|---|---|---|---|
| | Length of MC (day) | Length of MP (day) | Length of MC (day) | Length of MP (day) | Length of MC (day) | Length of MP (day) | Length of MC (day) | Length of MD (day) |
| Group 1 (Vehicle) | | | | | | | | |
| 96 | 27 | 2 | 25 | 3 | 28 | 2 | 27 | 2 |
| 126 | 25 | 1 | 24 | 2 | 26 | 2 | 24 | 2 |
| 204 | 29 | 3 | 28 | 2 | 30 | 3 | 27 | 3 |
| Group 2 (5 mg/week) | | | | | | | | |
| 246 | 26 | 4 | 24 | 2 | 39 | 5 | 27 | 4 |
| 232 | 28 | 1 | 27 | 1 | 29 | 1 | 31 | 3 |
| 250 | 24 | 3 | 26 | 1 | 26 | 1 | 27 | 4 |
| Group 3 (10 mg/week) | | | | | | | | |
| 208 | 26 | 4 | 25 | 3 | 53* | 1 | 26 | 4 |
| 210 | 24 | 2 | 26 | 1 | 25 | 1 | 48 | 1 |
| 180 | 30 | 3 | 28 | 1 | 28 | 2 | 27 | 3 |

*2 ovulation cycles in which bleeding was slight after the first cycle.

The above-described observations clearly show that competitive progesterone antagonists are suitable for contraception (implantation inhibition), at individual doses having a non-ovulation-inhibiting effect as well as a non-abortive effect in each individual dosage unit, provided the administration of the dosage units takes place before and optionally also after ovulation within each menstrual cycle.

As competitive progesterone antagonists, all compounds are suitable which have a great affinity to the gestagen receptor (progesterone receptor) and exhibit no gestagen activity of their own. For example, the following steroids are suitable:

11β-[(4-N,N-Dimethylamino)-phenyl]-17β-hydroxy-17α-propinyl-4,9(10)-estradien-3-one (RU-38486), 11β-[(4-N,N-dimethylamino)-phenyl]-17β-hydroxy-18-methyl-17α-propinyl-4,9(10)-estradien-3-one and Such competitive progesterone antagonists can also be designated as dissociated, since at a specific threshold dose, changes of the endometrium are observed, but the ovulation (central effect) is not inhibited. The ratio of ovulation-inhibiting and implantation inhibiting (dissociation factor) doses can be used as a measurement for the dissociation. It varies depending on the species and is about 30 or more for a dissociated competitive progesterone antagonist (in the rat after peroral administration) to be used according to the invention.

The advantage of dissociated competitive progesterone antagonists being used according to this invention lies in the fact that they can be administered at higher doses to ensure achieving the necessary endometrial effects without ovulation being inhibited; i.e., the "normal" course of the menstrual cycle is maintained.

The competitive progesterone antagonists can be administered, for example, locally, topically, enterally, transdermally or parenterally. Oral administration is preferred.

For the preferred oral administration, especially tablets, coated tablets, capsules, pills, suspensions or solutions are suitable, which can be produced in the usual way with the additives and vehicles usual in galenicals. For local or topical use, for example, vaginal suppositories, vaginal gels, implants, vaginal rings or transdermal systems such as skin plasters are suitable.

A dosage unit typically contains about 0.25 to 50 mg of 11β-[(4-N,N-dimethylamino)-phenyl]-17α-hydroxy-17β-(3-hydroxypropyl)-13α-methyl-4,9(10)-gonadien-3-one or a biologically equivalent amount of another competitive progesterone antagonist.

If the administration of the pharmaceutical agent produced according to the invention takes place by an implant, a vaginal ring or a transdermal system, these administration systems have to be designed so that the dose of the competitive progesterone antagonist released daily in this range is 0.25 to 50 mg.

The dose of a competitive progesterone antagonist to be administered according to the invention is below the ovulation inhibiting as well as abortion-inductive dose range of the progesterone antagonist in question.

In general, 0.25–20 mg is administered per one-time dose; especially and specifically in the use of peripherally selective competitive progesterone antagonists, 0.5–50 mg per one-time administration can be dosed, since the peripherally selective substances permit a far higher dosage without resulting in ovulation inhibition. The term, "one-time" dose or administration includes an administration system continuously releasing the competitive progesterone antagonist at a rate corresponding to a 0.25–20 mg daily dose or a 0.5–50 mg single dose.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of German priority applications P 42 16 003.0 and P 42 16 004.9, are hereby incorporated by reference.

PREPARATIVE EXAMPLE 1

11β,19-[4-(4-Cyanophenyl)-o-phenylene]-17β-hydroxy-17α-(3-hydroxyprop-1(Z)-enyl)-4-androsten-3-one a) 3,3-Dimethyltrimethylenedioxy-11β,19-(4-nonafluorobutylsulfonyloxy-o-phenylene)-androstane-5α,17β-diol 50 g of 3,3-dimethyltrimethylenedioxy-11β,19-(4-hydroxy-o-phenylene)-androstane-5α,17β-diol (Example 18a of PCT application PCT/DE88/00150 whose disclosure is incorporated herein by reference) is dissolved under protective gas in 1.75 l of tetrahydrofuran (slightly clouded solution) and mixed at 0° C. with 71.3 ml of n-butyllithium solution (1.6 m in hexane). After 30 minutes of stirring, 22.8 ml of 1,1,2,2,3,3,4,4,4-nonafluoro-1-butanesulfonyl fluoride (~90%) is instilled. After one hour of stirring with ice bath cooling, the reaction mixture is stirred into saturated sodium bicarbonate solution and intensively stirred for one more hour. Then, after adding ethyl acetate, the aqueous phase is separated and extracted several times with ethyl acetate. The combined organic phases are washed neutral with saturated sodium chloride solution, dried on sodium sulfate and concentrated by evaporation in a vacuum. 90.9 g of the title compound is obtained as crude product. 1.9 g of the thus produced nonaflate ($C_4F_9SO_3$) is chromatographed on silica gel with a mixture of ethyl acetate/hexane. 1.27 g of the pure title compound is obtained as white foam.

Melting point: 132–133° C.; $[\alpha]_D^{22}$=+15.4° ($CHCl_3$; c=0.525)

b) 3,3-Dimethyltrimethylenedioxy-5α-hydroxy-11β,19-(4-nonafluorobutylsulfonyloxy-o-phenylene)-androstan-17-one 63 g of chromium trioxide is added in portions at 0° C. to a mixture of 210 ml of pyridine and 600 ml of methylene chloride. Then, 89 g of the nonaflate produced under a), dissolved in 250 ml of methylene chloride, is instilled at the same temperature. Then, the reaction mixture is heated slowly to room temperature and stirred for 2 hours. After completion of the stirring, the supernatant phase is decanted and the residue is washed several times thoroughly with methylene chloride. The combined organic phases are substantially freed from the residual inorganic components by washing with 0.5 m sodium hydroxide solution, washed neutral with water, dried on sodium sulfate and concentrated by evaporation in a vacuum (removal of the pyridine by azeotropic distillation with toluene). By chromatography of the residue on aluminum oxide (neutral, step III) with a mixture of ethyl acetate/hexane, 61.9 g of the title compound is obtained as yellowish foam. Crystallization from ethyl acetate results in 55.7 g.

Melting point: 176–177° C.; $[\alpha]_D^{22}$=+25.3° ($CHCl_3$; c=0.520).

c) 3,3-Dimethyltrimethylenedioxy-11β,19-(4-nonafluorobutylsulfonyloxy-o-phenylene) -17α-[3-(tetrahydropyran-2-yloxy)-prop-1-inyl]-androstane-5α,17β-diol 1 l of absolute tetrahydrofuran is mixed at 0° C. under protective gas with 73.5 ml of 2-(2-propinyloxy)tetrahydro-2H-pyran. Then, 328 ml of a 1.6 m n-butyllithium solution (hexane) is instilled slowly in this solution without a sizeable temperature increase. After 30 minutes of stirring, a solution of 50 g of the ketone produced under b), dissolved in 500 ml of absolute tetrahydrofuran, is slowly instilled with ice bath cooling in this reaction mixture and allowed to stir for 30 more minutes. Then, the reaction mixture is mixed with saturated ammonium chloride solution and the aqueous phase is extracted with ethyl acetate. The combined organic phases are washed with sodium chloride solution, dried on sodium sulfate and concentrated by evaporation in a vacuum. The residue is chromatographed on aluminum oxide (neutral, step III). 50.3 g of the title compound is obtained as white foam.

d) 11β,19-[4-(4-Cyanophenyl)-o-phenylene]-3,3-dimethyltrimethylenedioxy-17α-[3-(tetrahydropyran-2-yloxy)-prop-1-inyl]-androstane-5α,17β-diol 50 g of the nonaflate produced under c) is dissolved in a mixture of 400 ml of toluene and 155 ml of ethanol and mixed in succession under protective gas with 1.44 g of tetrakis(triphenylphosphine)palladium(0), 5.33 g of lithium chloride, 78 ml of 2 m sodium carbonate solution and 13.1 g of 4-(1,3,2-dioxaborinan-2-yl)benzonitrile. S. Takahashi et al., Bul. Chem. Soc. Jpn., 62, 3896 (1989). The reaction mixture is then stirred for 3 hours at an oil bath temperature of 95° C., cooled to room temperature and mixed with water and ethyl acetate. The aqueous phase is separated and extracted with ethyl acetate. The combined organic phases are dried on sodium sulfate and concentrated by evaporation in a vacuum. The residue is chromatographed on silica gel with a mixture of ethyl acetate/hexane. 38 g of the title compound is obtained as yellowish foam.

$[\alpha]_D^{22}$ =−36.5° (CHCl$_3$, c=0.515)

e) 11β,19-[4-(4-Cyanophenyl)-o-pbenylene]-17β-hydroxy-17α-(3-hydroxyprop-1-inyl)-4-androsten-3-one 37 g of the ketone acetal produced under d) is dissolved in 950 ml of acetone and mixed under protective gas with 95 ml of 4 n aqueous hydrochloric acid. After two hours of stirring at 50° C., the reaction mixture is poured on cold saturated sodium bicarbonate solution (basic pH) and most of the acetone is distilled off. After adding methylene chloride, the aqueous phase is separated and extracted several times with methylene chloride. The combined organic phases are dried on sodium sulfate and concentrated by evaporation in a vacuum. The residue is chromatographed on silica gel with a mixture of ethyl acetate/hexane. 23.8 g of the title compound is obtained as yellowish foam.

f) 11β,19-[4-(4-Cyanophenyl)-o-phenylene]-17β-hydroxy-17α-(3-hydroxyprop-1(Z) -enyl) -4-androsten-3-one 23 g of the propargyl alcohol produced under e) is dissolved under protective gas in 825 ml of tetrahydrofuran, mixed with 23 ml of pyridine and hydrogenated using 2.3 g of palladium (10%) on barium sulfate as catalyst at standard pressure. After absorbing an equivalent of hydrogen (in addition to TLC control!), the reaction mixture is filtered on Celite, the filter residue is rewashed with tetrahydrofuran and the filtrate is concentrated by evaporation in a vacuum. The pyridine is removed by azeotropic distillation with toluene. The residue is recrystallized from acetone/tetrahydrofuran and the thus obtained crystallizate is recrystallized again from methylene chloride/methanol. 14.3 g of the title compound is obtained as white crystallizate.

Melting point: 265–266° C. (under decomposition); $[\alpha]_D^{22}$=+117.8° (CHCl$_3$, c=0.500).

PREPARATIVE EXAMPLE 2

11β,19-[4-(3-Pyridinyl)-o-phenylene]-17β-hydroxy-17α-(3-hydroxyprop-1(Z)-enyl)-4-androsten-3-one a) 11β,19-[4-(3-Pyridinyl)-o-phenylene]-3,3-dimethyltrimethylenedioxy-17α-[3-(tetrahydropyran-2-yloxy)-prop-1-inyl]-androstane-5α,17β-diol 13.7 g of the nonaflate produced under 1c) is dissolved in a mixture of 140 ml of toluene and 70 ml of ethanol and mixed in succession under protective gas with 877 mg of tetrakis(triphenylphosphine)palladium(0), 1.29 g of lithium chloride, 19 ml of 2 m sodium carbonate solution and 2.46 g of diethyl(3-pyridinyl)borane. The reaction mixture is then stirred for 2 hours at an oil bath temperature of 95° C., cooled to room temperature and mixed with water and ethyl acetate. The aqueous phase is separated and extracted with ethyl acetate. The combined organic phases are dried on sodium sulfate and concentrated by evaporation in a vacuum. The residue is chromatographed on silica gel with a mixture of ethyl acetate/hexane. 8.8 g of the title compound is obtained as yellowish foam.

b) 11β,19-[4-(3-Pyridinyl)-o-phenylene]-17β-hydroxy-17α-(3-hydroxyprop-1-inyl)-4-androsten-3-one 8.8 g of the ketone acetal produced under a) is dissolved in 250 ml of acetone and mixed under protective gas with 5 ml of 4 n aqueous hydrochloric acid. After two hours of stirring at 50° C., the reaction mixture is poured on cold saturated sodium bicarbonate solution (basic pH) and most of the acetone is distilled off. After adding methylene chloride, the aqueous phase is separated and extracted several times with methylene chloride. The combined organic phases are dried on sodium sulfate and concentrated by evaporation in a vacuum. The residue is chromatographed on silica gel with a mixture of ethyl acetate/hexane. 5.0 g of the title compound is obtained as yellowish foam.

$[\alpha]_D^{22}$=+48.6° (CHCl$_3$; C=0.530).

c) 11β,19-[4-(3-Pyridinyl)-o-phenylene]-17β-hydroxy-17α-(3-hydroxyprop-1(Z) -enyl)-4-androsten-3-one 5 g of the propargyl alcohol produced under b) is dissolved under protective gas in 200 ml of tetrahydrofuran, mixed with 5 ml of pyridine and hydrogenated using 500 mg of palladium (10%) on barium sulfate as catalyst at standard pressure. After absorbing an equivalent of hydrogen (in addition to TLC control!), the reaction mixture is filtered on Celite, the filter residue is rewashed with tetrahydrofuran and the filtrate is concentrated by evaporation in a vacuum. The pyridine is removed by azeotropic distillation with toluene. The residue is chromatographed on silica gel with a mixture of ethyl acetate/hexane. 3.4 g of the title compound is obtained as yellowish foam. Crystallization of ethyl acetate yields 3.12 g of white crystals.

Melting point: 219–221° C.; $[\alpha]_D^{22}$=+72.2° (CHCl$_3$, c=0.505).

FORMULATION EXAMPLE 3

10.0 mg of 11β-[(4-N,N-dimethylamino)-phenyl]-17α-hydroxy-17β-(3-hydroxypropyl)-13α-methyl-4,9(10)-gonadien-3-one
140.5 mg of lactose
69.5 mg of corn starch
2.5 mg of polyvinylpyrrolidone 25
2.0 mg of aerosil
0.5 mg of magnesium stearate 225.0 mg total weight Formulate the above composition into 10 mg. tablets for oral administration in a conventional manner.

For the use of the pharmaceutical agent produced according to the invention, it is critical that at least one dosage unit is administered in the follicular phase of the menstrual cycle (before the ovulation) and optionally at least one dosage unit is administered in the luteal phase of the menstrual cycle (after the ovulation).

Preferably, the pharmaceutical agent produced according to the invention is administered in individual dosage units every to 4 to every 10 days, preferably weekly or the same day, beginning on any day before ovulation occurs in the first administration menstrual cycle. The time intervals between administration of the individual dosage units preferably are constant.

Preferably, the pharmaceutical agent according to the invention is administered once each week, on the same day of the week, for example on Mondays ("Monday pill"). By the weekly administration rhythm always on the same day of the week, a high degree of reliability is assured. However, it is also possible to administer a dosage unit daily, every 2 days or every 3 days, either during only the follicular phase or additionally also in the luteal phase of the menstrual cycle. It is also possible to vary the intervals between the administration of the individual dosage units of the pharmaceutical agent according to the invention or to administer it constantly from an implanted slow release vehicle.

To determine the ovulation-inhibiting doses of competitive progesterone antagonists, the ovulation-inhibiting test described below is performed on the rat; the respective abortively effective doses follow from the known (e.g., U.S. Pat. No. 5,095,129) rat abortive test.

The determined dissociation factors for Compounds I, II and RU 486 are

| Compound | Dissociation factor |
| --- | --- |
| I | >100 |
| II | >30 |
| RU 486 | <10 |

For both compounds I and II, it further has been found that with extraordinarily strong antinidatory effectiveness (compound I is still completely implantation-inhibiting effective in the rat at a daily dose of 0.1 mg and compound II at a daily dose of 0.3 mg), they are not simultaneously antiglucocorticoidally effective. This is seen from the thymolysis test for antiglucocorticoidal effect (EP-A-0 283 428).

The production of compounds I and II takes place according to the synthesis route described in EP-A-0 283 428 and as is indicated in the examples below.

Ovulation Inhibition Test on the Rat

Principle of the method

For detection of ovulation-inhibiting substances, the rat is well-suited insofar as it spontaneously ovulates and the cycle can easily be observed by means of vaginal smears. This makes it possible to control the course of the test also during the treatment phase.

METHOD EXAMPLE 4

Test Animals

Female rats weighing 190–210 g, pro dosi 6 animals.

The animals are kept in Macrolon cages in rooms with controlled exposure to light (10 hours of darkness: 14 hours of brightness), fed a standard diet (pelletized rat food) and tap water at will.

Formulation and Administration of the Test Substance

The test substances are dissolved in benzyl benzoate/castor oil (1+9 v/v) and the daily dose is administered in a volume of 0.2 ml s.c.

In the oral application, the test substance is suspended in a carrier liquid (85 mg of Myrj® in 100 ml of 0.9% w/v NaCl solution) and the daily dose is administered in a volume of 0.5 ml.

Test Batch

Two cycles are observed before the beginning of the test by means of vaginal smears. Only animals with a regular 4-day cycle are used in the test. The assignment to the treatment groups takes place at random. Beginning in the metestrus, the test substance is administered over 4 days (day 1–4) and the cycle is further controlled.

On day 4 (after the administration), animals, which have an estrus or metestrus at the time of the vaginal smear, are ovariectomized on one side under ether anesthesia. Crush preparations are prepared from the tubes and examined by microscope for the presence of egg cells. On day 5, all animals (intact and unilaterally ovariectomized) are killed with $CO_2$ gas and the tubes are prepared and examined in the same way.

METHOD EXAMPLE 5

Evaluation

In the individual dosage groups, the percentage of animals in which the ovulation was inhibited is determined.

Volunteers

Anamnestic condition of patients: Healthy, normocyclic women only. Preferably volunteers after ligation of both fallopian tubes or after surgical extirpation of both fallopian tubes (ectopic pregnancies), or women only exposed to vasectomized partners.

Human Study 1: Characterization of the biochemical and morphological marker(s) of endometrial receptivity after short-term treatment with onapristone during the luteal phase.

This is a pilot study to establish which biochemical methods, in particular identification of endometrial marker proteins, are useful in monitoring further studies with low-dose onapristone (daily and intermittent).

Experimental Protocol

Groups of Volunteers

Two groups (control and treatment group) of 8–10 women, each.

Duration of the Study

Evaluation of three cycles: pre-treatment, treatment and post-treatment cycles.

TREATMENT: 50 mg onapristone/day on days LH+1 and LH+2 orally

This dose of onapristone is known to induce premature menstruation in humans when given during the late luteal phase. However, according to the Bygdeman's study (Swahn et al. (1990)), early luteal treatment (LH+2) with a single dose of 200 mg RU 486 does not impair the length of the cycle.

EVALUATION: RIA: LH, FSH, E2 and progesterone during the pre-treatment, treatment and post-treatment cycles.

Endometrial biopsy and collection of the uterine fluid on day LH+3 and day LH+8 (treatment cycle) (see Appendix for details)

Occurrence of menstrual bleeding.

Human Study 2: Evaluation of daily application of onapristone on ovulation and endometrial morphology and biochemistry: a dose-finding study.

a) Objective

The results of this study identifies a dose of onapristone which does not impair the cycle but does exhibit an effect on the morphology and function (endometrial marker proteins) of the endometrium. A minimal dose inducing endometrial changes can thus be established.

b) Design of Study

Groups of volunteers: Four groups (three treatment groups and a control group) of 8–10 women each.

Duration of the study: Evaluation of three cycles: pre-treatment, treatment and post-treatment cycles.

Regimen: 18 daily oral administration of 20 mg (group 1), 10 mg (group 2) and 5 mg (group 3) onapristone starting on day 1 of the cycle.

c) Evaluation

RIA, LH, FSH, $E_2$ and progesterone and cortisol during the pre-treatment, treatment and post-treatment cycles.

Evaluation of endometrial biopsies and collection of the uterine fluid (by prevical) on day 16 and day 23 of the treatment cycle (see appendix for details)

Occurrence of menstrual bleeding.

Human Study 3: Effects of once-a-week administration of onapristone on ovulation, endometrial morphology and biochemistry a) Objective The results of this study determines a once-a-week dose of onapristone which does not impair the cycle but does exhibit an effect on the morphology and function (endometrial marker proteins) of the endometrium.

b) Design of Study

Groups of volunteers: Four groups (five treatment groups and a control group) of 8–10 women with ligated oviducts.

Duration of the study: Evaluation of four cycles: pretreatment, two treatment and post-treatment cycles.

Treatment

Once-a-week oral administration of 50 mg (group 1) 20 mg (group 2), 10 mg (group 3) 2 mg (group 5) and 0.25 mg (group 5), onapristone starting on day 1 of the cycle over the two cycles.

c) Evaluation

RIA, LH, FSH, $E_2$ and progesterone during the pretreatment, treatment and post-treatment cycles.

Evaluation of endometrial biopsies and collection of the uterine fluid on day 16 and day 23 of both treatment cycles (see appendix for details).

Occurrence of menstrual bleeding and cycle abnormalities:

By performing the described treatment scheme, the following is observed: better control of the cycle of the treatment groups compared to the control group; high tolerance; high contraception reliability; and estrogen-free oral contraception.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of contraception in a female, which comprises administering thereto during her menstrual cycle an amount of a competitive progesterone antagonist, which is less than an ovulation-inhibiting dose and less than an abortion-inductive dose.

2. A method according to claim 1, wherein the competitive progesterone antagonist is administered during both the follicular phase and the luteal phase.

3. A method according to claim 2, wherein the progesterone antagonist is administered orally about one weekly during each week of the menstral cycle.

4. A method according to claim 1, wherein the competitive progesterone antagonist is 11β-[(4-N,N-Dimethylamino)-phenyl]-17β-hydroxy-17α-propinyl-4,9(10)-estradien-3-one (RU 38486), 11β-[(4-N,N-dimethylamino)-phenyl]-17β-hydroxy-18-methyl-17α-propinyl-4,9(10)-estradien-3-one, 11β-[(4-N,N-dimethylamino)-phenyl]-17aβ-hydroxy-17aαpropinyl-D-homo-4,9(10),16-estratrien-3-one, 11β-p-methoxyphenyl-17β-hydroxy-17α-ethinyl-4,9 (10)-estradien-3-one, or 11β-(4-acetylphenyl)-17β-hydroxy-17α-(prop-1-inyl)-4,9(10)-estradien-3-one.

5. A method according to claim 1, wherein the competitive progesterone antagonist is 11β-(4-Dimethylaminophenyl)-17α-hydroxy-17β-(3-hydroxypropyl)-13α-methyl-4,9-gonadien-3-one, or 11β-(4-acetylphenyl)-17β-hydroxy-17α-(3-hydroxyprop-1-enyl)-4,9(10)-estradien-3-one.

6. A method according to claim 1, wherein the competitive progesterone antagonist is 11β,19-[4-(cyanophenyl)-o-phenylene]-17β-hydroxy-17α-(3-hydroxyprop-1(Z)-enyl)-4-androsten-3-one, or 11β,19-[4-(3-pyridinyl)-o-phenylene]-17β-hydroxy-17α-(3-hydroxyprop-1(Z)-enyl)-4-androsten-3-one.

7. A method according to claim 1, wherein the progesterone antagonist is administered in individual dosage units every 4 to every 10 days, beginning on any day before the day of ovulation of the first menstrual cycle during which the administration occurs.

8. A method according to claim 1, wherein the progesterone antagonist is administered orally.

9. A method according to claim 1, wherein the female is a human being.

10. A method according to claim 1, wherein the female is a human being and the progesterone antagonist is administered thereto orally every week of each menstrual cycle during which contraception is desired.

11. A method according to claim 10, wherein the competitive progesterone antagonist is 11β,19-[4-(cyanophenyl)-o-phenylene]-17β-hydroxy-17α-(3-hydroxyprop-1(Z)-enyl)-4-androsten-3-one, or 11β,19-[4-(3-pyridinyl)-o-phenylene]-17β-hydroxy-17α-(3-hydroxyprop-1(Z)-enyl)-4-androsten-3-one.

12. A method of contraception in a female, which comprises administering thereto during her menstrual cycle an amount of a competitive progesterone antagonist, which is less than an ovulation-inhibiting dose and less than an abortion-inductive dose and which is effective to inhibit the formation of endometrial glands and epithelium growth.

* * * * *

UNITED STATES PATENT AND TRADEMARK OFFICE
CERTIFICATE OF CORRECTION

PATENT NO. : 6,340,688 B1
DATED : January 22, 2002
INVENTOR(S) : Krzystof Chwalisz et al.

It is certified that error appears in the above-identified patent and that said Letters Patent is hereby corrected as shown below:

Column 13,
Line 52, reads "one" should read -- once --
Line 53, reads "menstral" should read -- menstrual --

Column 14,
Line 8, reads "17aαpropinyl" should read -- 17aα-propinyl --

Signed and Sealed this

Fifth Day of April, 2005

JON W. DUDAS
*Director of the United States Patent and Trademark Office*